(12) United States Patent
Hazama

(10) Patent No.: US 10,779,840 B2
(45) Date of Patent: Sep. 22, 2020

(54) HEMOSTATIC DEVICE

(71) Applicant: TERUMO KABUSHIKI KAISHA, Tokyo (JP)

(72) Inventor: Kenichi Hazama, Bear, DE (US)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 188 days.

(21) Appl. No.: 16/137,769

(22) Filed: Sep. 21, 2018

(65) Prior Publication Data
US 2019/0046214 A1 Feb. 14, 2019

Related U.S. Application Data

(63) Continuation of application No. PCT/JP2017/011494, filed on Mar. 22, 2017.

(30) Foreign Application Priority Data

Mar. 23, 2016 (JP) .................................. 2016-058218

(51) Int. Cl.
*A61B 17/135* (2006.01)
*A61B 17/132* (2006.01)
(Continued)

(52) U.S. Cl.
CPC ........ *A61B 17/135* (2013.01); *A61B 17/1325* (2013.01); *A61B 2017/00778* (2013.01); *A61B 2017/12004* (2013.01); *A61F 5/34* (2013.01)

(58) Field of Classification Search
CPC .. A61F 2013/00468; A61F 2013/00182; A61F 2013/00617; A61F 2013/00829;
(Continued)

(56) References Cited

U.S. PATENT DOCUMENTS 3,633,567 A 1/1972 Sarnoff
5,234,459 A * 8/1993 Lee ...................... A61B 17/135
606/202
(Continued)

FOREIGN PATENT DOCUMENTS

JP S5146989 B1 12/1976
JP S61217132 A 9/1986
(Continued)

OTHER PUBLICATIONS

European Search Report dated Nov. 26, 2019 issued by the European Patent Office in European Patent Application No. 17770283.4 (6 pages).
(Continued)

*Primary Examiner* — Elizabeth Houston
*Assistant Examiner* — Socrates L Boutsikaris
(74) *Attorney, Agent, or Firm* — Buchanan Ingersoll & Rooney PC

(57) ABSTRACT

A hemostatic device can inflate an inflatable portion without using a separate dedicated instrument, can reduce an unpleasant feeling of a wearer, and can prevent a site where bleeding is to be stopped from being unintentionally and unnecessarily compressed. The hemostatic device has a band for being wrapped around a limb, an inflatable portion that is inflated by injecting gas, an injection part that is configured to inject gas into the inflatable portion, and a flow route that permits communication between the inflatable portion and the injection part. The flow route includes a backflow preventer which prevents gas from flowing out to the injection part from the inflatable portion. The injection part is located on the band, and includes holes which penetrate the injection part in a direction intersecting a perpendicular line to a region of the band where the injection part is located.

17 Claims, 14 Drawing Sheets

(51) Int. Cl.
*A61B 17/00* (2006.01)
*A61B 17/12* (2006.01)
*A61F 5/34* (2006.01)

(58) Field of Classification Search
CPC . A61F 5/05866; A61F 5/34; A61M 2025/026; A61M 2025/0206; A61M 2025/028; A61B 17/1325; A61B 17/135; A61B 17/132; A61B 17/1322; A61B 17/085; A61B 2017/12004; A61B 2017/00902; A61B 2017/22059; A61B 2017/00778; A61B 5/6824
USPC .............. 601/33, 40, 132, 151; 606/201–203
See application file for complete search history.

(56) References Cited

U.S. PATENT DOCUMENTS

| | | | |
|---|---|---|---|
| 5,509,423 A * | 4/1996 | Bryars | A61B 5/025 600/503 |
| 5,649,954 A | 7/1997 | McEwen | |
| 2015/0032149 A1* | 1/2015 | Croushorn | A61B 17/135 606/202 |
| 2015/0119773 A1 | 4/2015 | Flannery et al. | |

FOREIGN PATENT DOCUMENTS

| | | |
|---|---|---|
| JP | H11512630 A | 11/1999 |
| JP | 2010029291 A | 2/2010 |
| JP | 2014521368 A | 8/2014 |
| WO | 98046144 A1 | 10/1998 |
| WO | 2011001431 A1 | 1/2011 |
| WO | 2014167422 A2 | 10/2014 |
| WO | 2015/060967 A1 | 4/2015 |

OTHER PUBLICATIONS

Office Action (Examination report No. 1) dated Dec. 19, 2018, by the Australian Patent Office in corresponding Australian Patent Application No. 2017237281. (3 pages).

An English Translation of the International Search Report (Form PCT/ISA/210) and the Written Opinion of the International Searching Authority (Form PCT/ISA/237) dated Jun. 27, 2017 by the Japanese Patent Office in corresponding International Application No. PCT/JP2017/011494 (9 pages).

International Search Report (PCT/ISA/210) dated Jun. 27, 2017, by the Japan Patent Office as the International Searching Authority for International Application No. PCT/JP2017/011494.

Written Opinion (PCT/ISA/237) dated Jun. 27, 2017, by the Japan Patent Office as the International Searching Authority for International Application No. PCT/JP2017/011494.

* cited by examiner

HEMOSTATIC DEVICE

CROSS-REFERENCES TO RELATED APPLICATIONS

This application is a continuation of International Application No. PCT/JP2017/011494 filed on Mar. 22, 2017 which claims priority to Japanese Application No. 2016-058218 filed on Mar. 23, 2016, the entire content of both of which is incorporated herein by reference.

TECHNICAL FIELD

The present invention generally relates to a hemostatic device used for performing hemostasis by compressing a punctured site.

BACKGROUND DISCUSSION

In recent years, percutaneous treatment and examination have been performed in which a blood vessel in the arms or legs is punctured and an introducer sheath is introduced into a puncture site so as to deliver a medical device such as a catheter to a lesion area via a lumen of the introducer sheath. In a case where this treatment and examination are performed, an operator needs to perform hemostasis in the puncture site after the introducer sheath is removed from the puncture site. In order to perform this hemostasis, a hemostatic device is known which includes a band for being wrapped around a limb such as arms and legs, means for securing the band in a state where the band is wrapped around the limb, and an inflatable portion that is located between the band and the limb, that is inflated by injecting a fluid into the inflatable portion and that compresses the puncture site.

When this hemostatic device is used, a physician or a nurse generally connects a dedicated instrument such as a syringe separate from the hemostatic device to a port which communicates with the inflatable portion of the hemostatic device, and injects the fluid into the inflatable portion by using the dedicated instrument, thereby inflating the inflatable portion of the hemostatic device.

In contrast, according to the hemostatic device disclosed in Japanese Patent Application Publication No. 2014-521368, an injection part (pressurizing pump) capable of injecting the gas into the inflatable portion is attached. Specifically, the injection part has a storage space capable of storing the gas and a hole part communicating with the storage space for fetching the gas. If the injection part is crushed (contracted) in a state where the hole part is closed by a finger, the gas stored inside the injection part is injected into the inflatable portion. The inflatable portion can be inflated by the injection part attached to the inflatable portion. Accordingly, the physician or the nurse can save labor and time for carrying the separate dedicated instrument or labor and time for connecting the separate dedicated instrument to the hemostatic device. In addition, it is possible to prevent a disadvantageous situation where the fluid cannot be injected into the inflatable portion due to a loss of the dedicated instrument.

SUMMARY

However, according to the hemostatic device disclosed in Japanese Patent Application Publication No. 2014-521368, the injection part is disposed in a state of protruding from the band to the limb side such as the arms and the legs. The injection part interferes with bending movement of the arms and the legs, or the injection part comes into contact with the limb, thereby causing a possibility that a wearer may have an unpleasant feeling.

In order to reduce the unpleasant feeling of the wearer, it is conceivable that the injection part may be located on the band. However, in this case, if the hole part is disposed at a position facing the band, a pressing force is transmitted to the puncture site via the band when the injection part is crushed while the hole part is closed by the finger, thereby causing a possibility that the puncture site may be unintentionally and unnecessarily compressed. In addition, if the hole part is disposed at the position facing the band, the hole part is likely to come into contact with surrounding objects. If the injection part is crushed and contracted in a state where the hole part is closed by coming into contact with the surrounding objects, the gas is unintentionally injected into the inflatable portion, thereby causing a possibility that the puncture site may be unnecessarily compressed.

The hemostatic device disclosed here can inflate an inflatable portion without using a separate dedicated instrument, which can reduce an unpleasant feeling of a wearer, and which can prevent a site where bleeding is to be stopped from being unintentionally and unnecessarily compressed.

The disclosed hemostatic device comprises: a band for being wrapped around a portion of a limb at which is located a site where bleeding is to be stopped; means for securing the band in a wrapped state in which the band is wrapped around the limb; an inflatable portion that is inflatable upon injecting gas into the inflatable portion and that compresses the site where bleeding is to be stopped when the inflatable portion is inflated; an injection part that includes a storage space configured to store the gas to be injected into the inflatable portion and that is configured to inject the gas into the storage space; and a flow route configured to communicate the inflatable portion and the injection part with each other. The flow route includes a backflow check structure which prevents the gas from flowing out to the injection part from the inflatable portion. The injection part is located on the band and includes a hole which communicates with the storage space and which penetrates the injection part in a direction intersecting a perpendicular line that is perpendicular to a region of the band where the injection part is located.

According to the hemostatic device configured as described above, the gas is injected into the inflatable portion by the injection part communicating with the inflatable portion. Therefore, a physician or a nurse can inflate the inflatable portion without using a separate dedicated instrument. In addition, the injection part is located on the band, and is less likely to come into contact with the limb. Accordingly, it is possible to reduce an unpleasant feeling of a wearer. In addition, the hole part penetrates the injection part in the direction intersecting the perpendicular line to the region of the band where the injection part is located. Therefore, a direction of a pressing force acting when the injection part is crushed in a state where the hole part is closed by a finger is the direction intersecting the perpendicular line to the band. Accordingly, the pressing force is less likely to be transmitted via the band to the site where bleeding is to be stopped. In addition, there is a low possibility that the hole part may be closed by coming into contact with surrounding objects. Accordingly, there is a low possibility that air may be injected into the inflatable portion after the injection part is crushed in a state where the hole part is unintentionally closed. Therefore, the hemostatic device according to the present invention can suitably prevent a disadvantageous situation in which the site where bleeding is to be stopped is unnecessarily compressed.

In accordance with another aspect, a hemostatic device comprises: a band configured to be wrapped around a portion of a limb at which is located a site where bleeding is to be stopped; means for securing the band in a wrapped state where the band is wrapped around the limb; an inflatable portion that is inflatable upon injecting gas into the inflatable portion and that compresses the site where bleeding is to be stopped when the inflatable portion is inflated; an injection part that includes a storage space configured to store the gas to be injected into the inflatable portion and that is configured to inject the gas into the storage space; a lumen extending between the inflatable portion and the injection part to communicate the inflatable portion with the injection part; and a backflow preventer that prevents the gas in the inflatable portion from flowing to the injection part by way of the lumen. The injection part includes a bottom face part secured to an outer surface of the band that faces away from the limb when the band is in the wrapped state, and the injection part includes two spaced apart through holes communicating the storage space with a region outside the storage space. The two through holes face each other at positions farther away from the band than the bottom face part.

According to another aspect, a method comprises: wrapping a band around a portion of a limb at which is located a site where bleeding is to be stopped so that an inflatable portion overlies the site and is positioned between the limb and an inner surface of the band that faces the limb; securing the band in a wrapped state around the limb while the inflatable portion remains overlying the site and positioned between the limb and the band; and applying a pressing force to an injection part that is in communication with the inflatable portion to compress the injection part and cause gas in the injection part to flow into the inflatable portion to inflate the inflatable portion and apply a compressive force to the site where bleeding is to be stopped. The injection part is fixed to the outer surface of the band that faces away from the limb in the wrapped state of the band. The applying of the pressing force to the injection part comprises applying the pressing force to opposite sides of the injection part in a direction intersecting a line perpendicular to the band.

BRIEF DESCRIPTION OF THE DRAWINGS

FIG. 6(A) is a view illustrating a state where air is injected into an inflatable portion, and FIG. 6(B) is a view illustrating a state where the inflatable portion is completely inflated.

FIG. 13(A) is a view illustrating a first sheet configuring the inflatable portion, and FIG. 13(B) is a view illustrating a second sheet configuring the inflatable portion.

DETAILED DESCRIPTION

Set forth below with reference to the accompanying drawings is a detailed description of embodiments of a hemostatic device representing examples of the inventive hemostatic device disclosed here. The dimensions or scales on the drawings may be exaggerated or different from actuality/reality for convenience of description and illustration. The following description also does not limit the technical scope or the meaning of terms described in appended claims.

Hereinafter, a hemostatic device 10 according to one embodiment will be described with reference to FIGS. 1 to 11. FIGS. 1 to 6 are views for describing each portion of the hemostatic device 10. FIGS. 7 to 11 are views for describing an example of using the hemostatic device 10.

Figure 7:
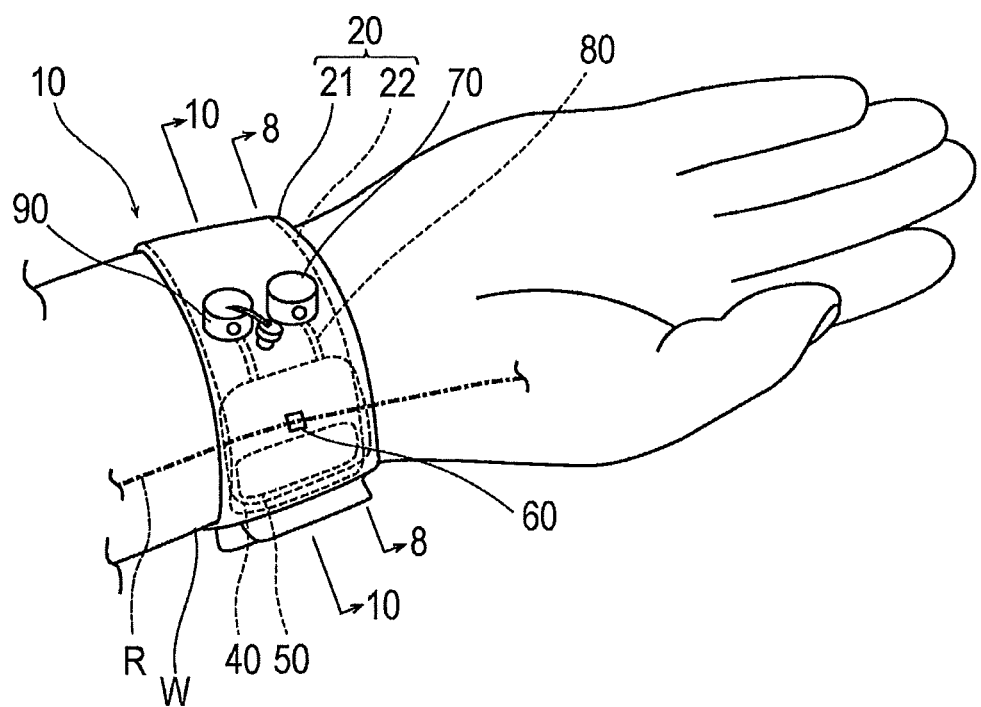
FIG. 7 is a schematic perspective view illustrating a state where the hemostatic device according to the embodiment is worn on a wrist.
Figure 9:
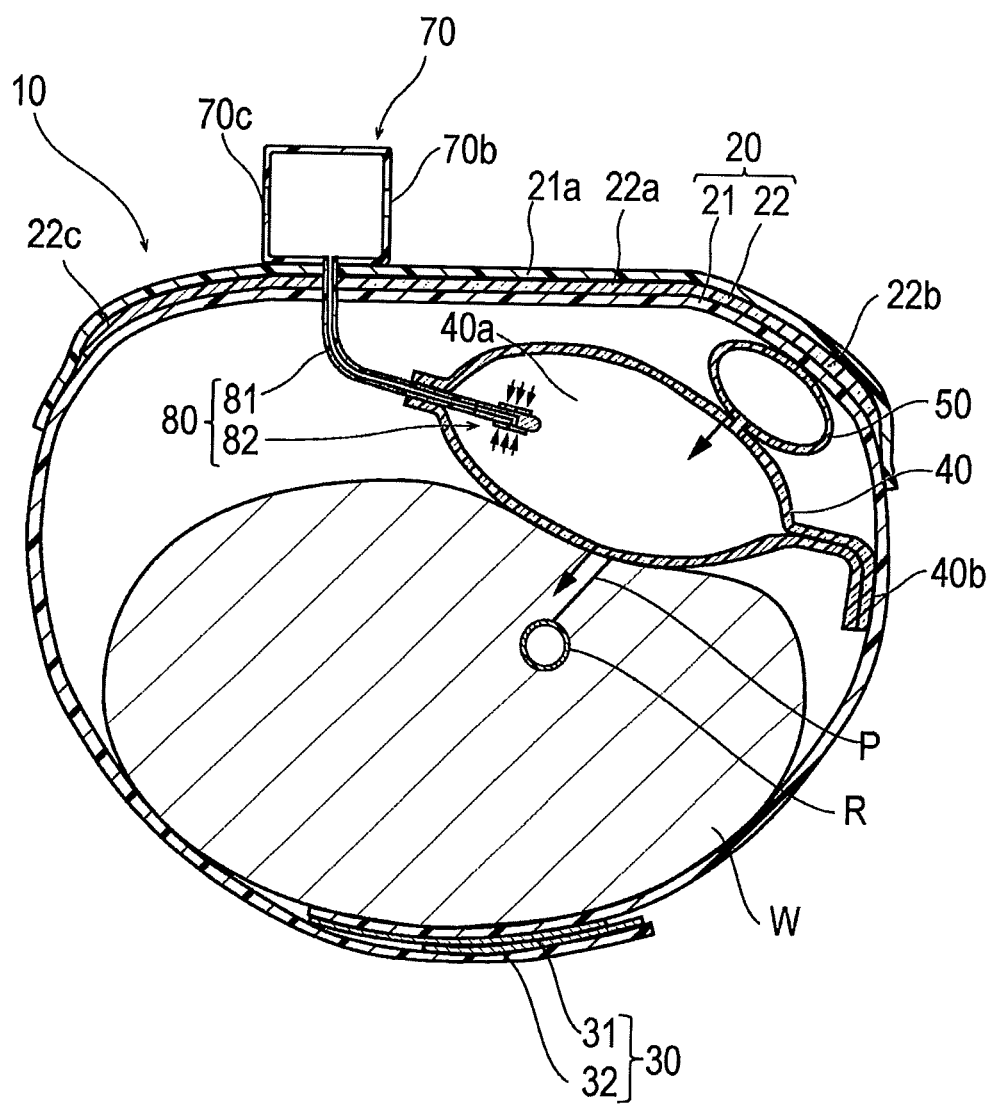
FIG. 9 is a cross-sectional view taken along line 8-8 in FIG. 7, and is a view illustrating a state where the inflatable portion is completely inflated.

As illustrated in FIGS. 7 and 9, the hemostatic device 10 is used for performing hemostasis on a puncture site P (corresponding to a "site where bleeding is to be stopped") formed in a radial artery R of a wrist W (corresponding to a "limb") in order to insert a catheter for performing treatment and examination into a blood vessel, after an introducer sheath indwelling the puncture site P is removed.

Figure 1:
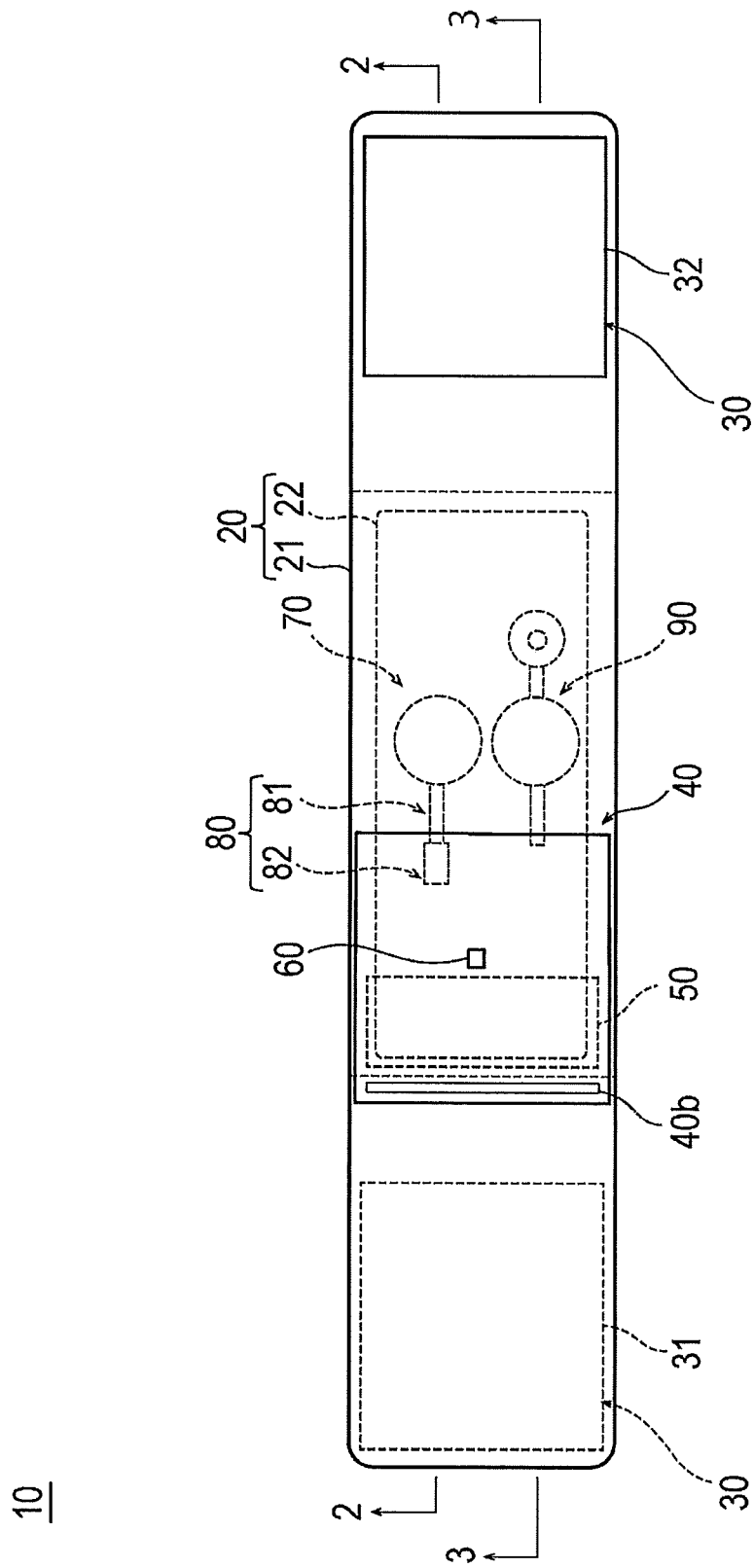
FIG. 1 is a plan view when a hemostatic device according to an embodiment is viewed from an inner surface side.
Figure 2:
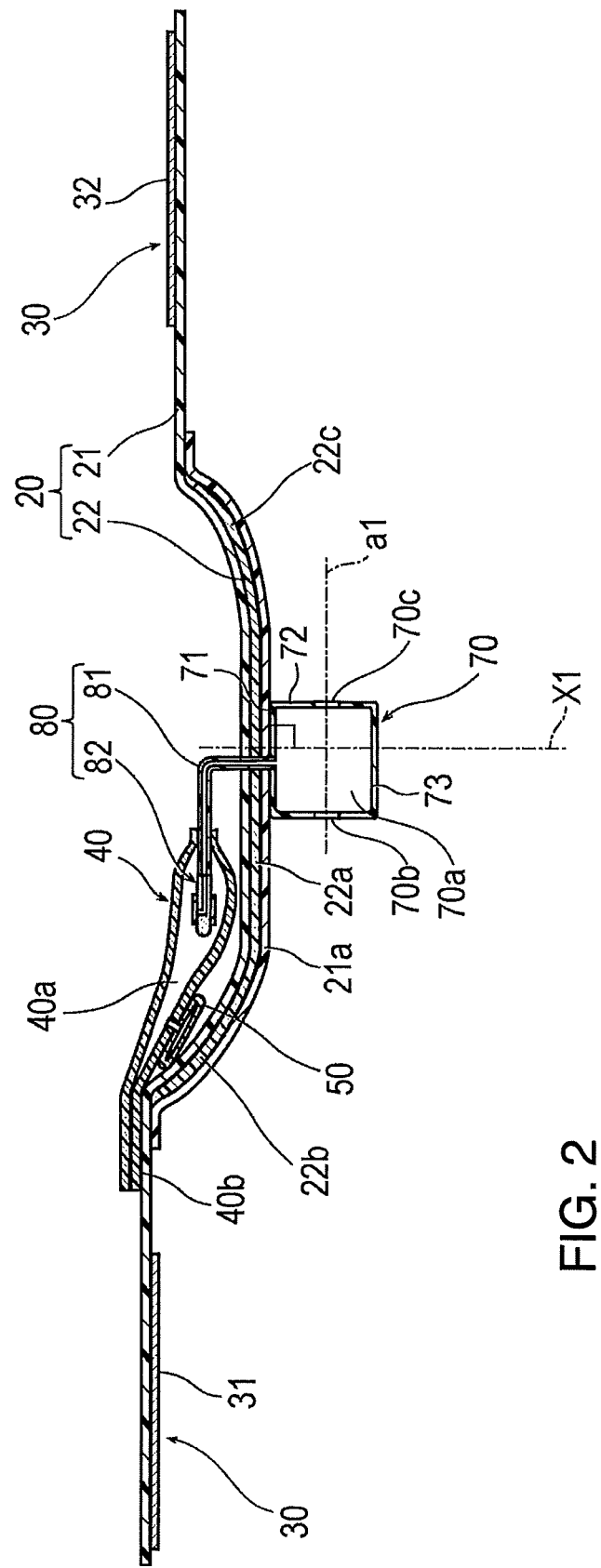
FIG. 2 is a cross-sectional view taken along line 2-2 in FIG. 1.
Figure 3:
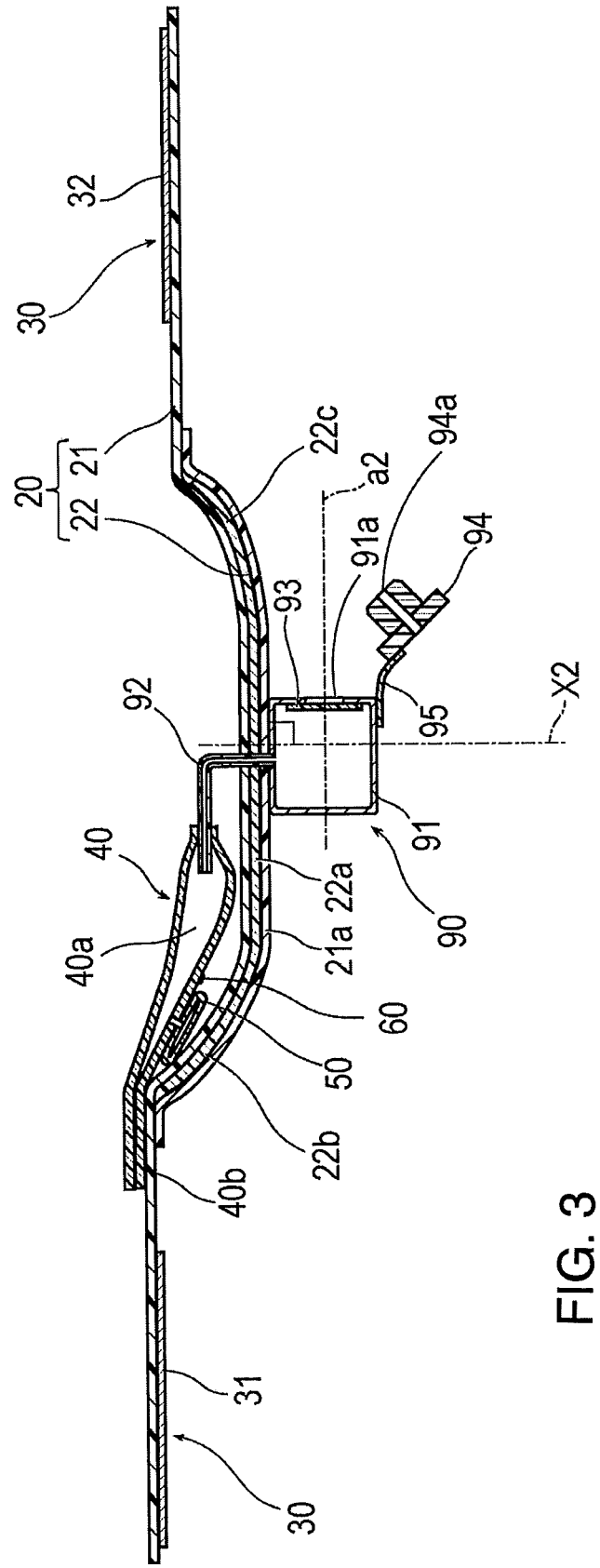
FIG. 3 is a cross-sectional view taken along line 3-3 in FIG. 1.

As illustrated in FIGS. 1 to 3, the hemostatic device 10 includes a band 20 for being wrapped around the wrist W, a surface fastener 30 (an example of "means for securing") for securing the band 20 in a state where the band 20 is wrapped around the wrist W, an inflatable portion 40 that is inflated by injecting air (an example of "gas") so as to compress or apply a compressive force to the puncture site P, an auxiliary compression portion 50 disposed between the inflatable portion 40 and the band 20, a marker 60 for aligning the inflatable portion 40 with the puncture site P, an injection part 70 that can inject air into the inflatable portion 40 and the auxiliary compression portion 50, a flow route 80 that causes the inflatable portion 40 and the injection part 70 to communicate with each other, and a discharge portion 90 through which air contained inside the inflatable portion 40 is discharged outward.

In the description which follows, when the band 20 is in a state of being wrapped around the wrist W, a surface (wearing surface) having the inflatable portion 40 located in the band 20 and facing a body surface side of the wrist W will be referred to as an "inner surface" (corresponding to a "first surface"), and a surface opposite the inner surface will be referred to as an "outer surface" (corresponding to a "second surface").

The band 20 includes a belt 21 configured to include a flexible belt-shaped member, and a support plate 22 which is more rigid than the belt 21.

Figure 8:
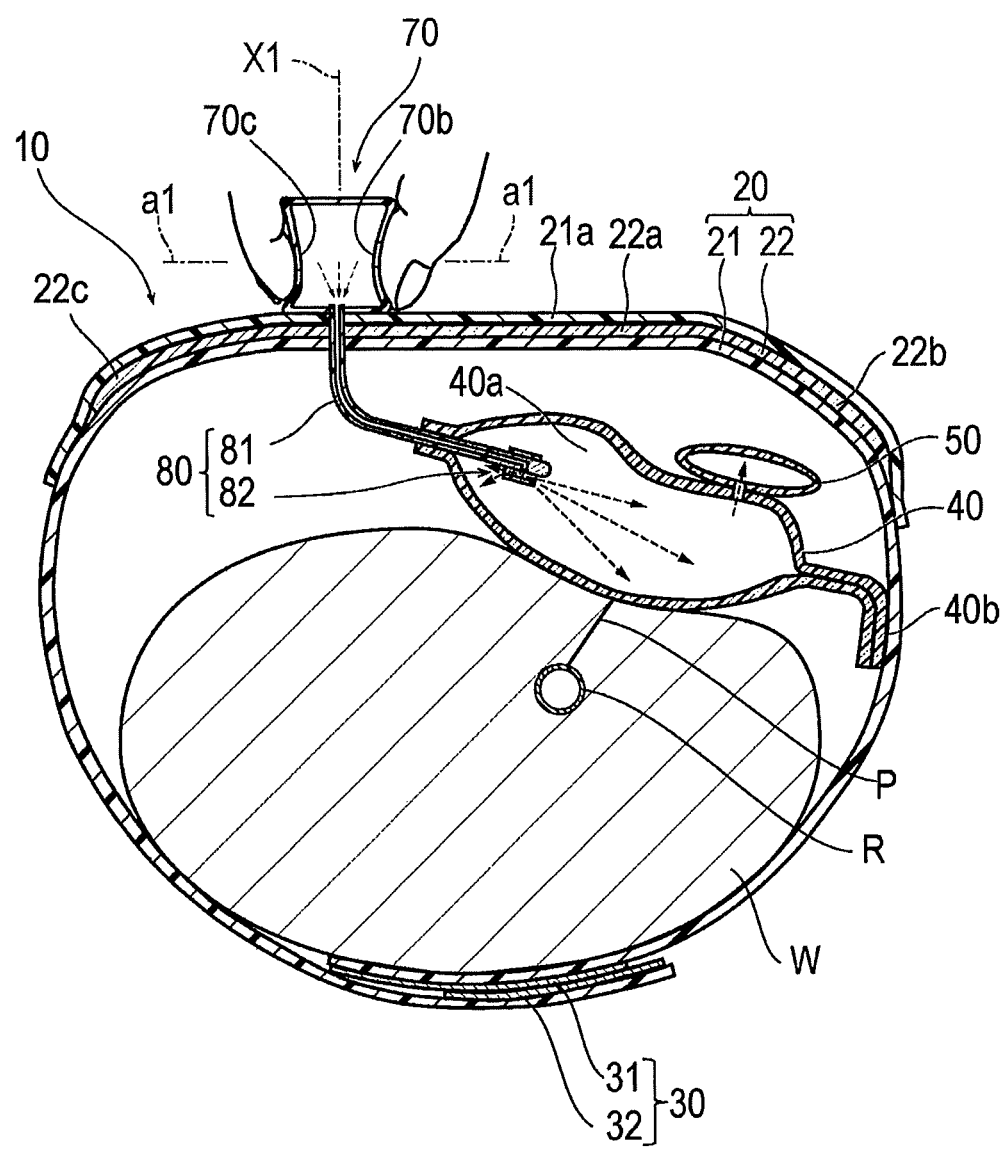
FIG. 8 is a cross-sectional view taken along line 8-8 in FIG. 7, and is a view illustrating a state where the inflatable portion is inflated.

As illustrated in FIGS. 7 and 8, the belt 21 is wrapped substantially one round around the outer periphery of the wrist W. As illustrated in FIG. 2, a support plate holder 21a for holding the support plate 22 is formed in a central portion of the belt 21. The support plate holder 21a may have a double structure construction (e.g., dual material layers) in such a way that a separate belt-like member may be joined to the outer surface side (or the inner surface side) by welding (heat-welding, high frequency welding, or ultrasound welding) or adhesion (adhesion using an adhesive or a solvent), thereby holding the support plate 22 inserted into a gap between the double structure construction.

A male side (or a female side) 31 of the surface fastener 30 generally called a Magic Tape® (registered trademark) is located on the outer surface side of a portion in the vicinity of the left end in FIG. 1 of the belt 21, and a female side (or a male side) 32 of the surface fastener 30 is located on the inner surface side of a portion in the vicinity of the right end in FIG. 1 of the belt 21. As illustrated in FIG. 8, the belt 21 is wrapped around the wrist W, and the male side 31 and the female side 32 are joined to each other. In this manner, the band 20 is worn on the wrist W and held on the wrist W. Without being limited to the surface fastener 30, other examples of means for securing the band 20 in a state where the band 20 is wrapped around the wrist W may be a snap, a button, a clip, or a frame member passing through the end portion of the belt 21.

The material from which the belt 21 is fabricated is not particularly limited, as long as the material is flexible. For example, this material includes polyvinyl chloride, polyolefin such as polyethylene, polypropylene, polybutadiene, and ethylene-vinyl acetate copolymer (EVA), polyester such as polyethylene terephthalate (PET) and polybutylene terephthalate (PBT), various thermoplastic elastomers such as polyvinylidene chloride, silicone, polyurethane, polyamide elastomer, polyurethane elastomer, and polyester elastomer, or any optional combination thereof (blend resin, polymer alloy, and laminate).

In addition, it is preferable that a portion overlapping at least the inflatable portion 40 in the belt 21 is substantially transparent. However, without being limited to transparency, the portion may be translucent or colored transparent. In this manner, the puncture site P is visible from the outer surface side, thereby enabling the marker 60 (to be described later) to easily align with the puncture site P.

As illustrated in FIG. 2, the support plate 22 is inserted into or positioned in the support plate holder 21a formed to have the double structure construction (e.g., two material layers) in the belt 21. In this manner, the support plate 22 is held by the belt 21. The support plate 22 has a plate shape in which at least a portion of the support plate 22 is curved toward the inner surface side (wearing surface side). The support plate 22 is configured to include a material which is more rigid than that of the belt 21 (i.e., the support plate may be made of a material more rigid than the belt 21), and is adapted or configured to maintain a substantially constant shape.

The support plate 22 has an elongated shape in a longitudinal direction of the belt 21. A central portion 22a in the longitudinal direction of the support plate 22 may be hardly curved (i.e., may exhibit virtually no curve), and has a flat plate shape. The portions of the support plate 22 on both sides of the central portion 22a include a first curved portion 22b (left side in FIG. 2) and a second curved portion 22c (right side in FIG. 2) which are curved toward the inner surface side and along the longitudinal direction (circumferential direction of the wrist W) of the belt 21.

Examples of the material which may be sued to fabricate the support plate 22 include acrylic resin, polyvinyl chloride (particularly, rigid polyvinyl chloride), polyolefin such as polyethylene, polypropylene, and polybutadiene, polystyrene, poly-(4-methylpentene-1), polycarbonate, ABS resin, polymethyl methacrylate (PMMA), polyacetal, polyacrylate, polyacrylonitrile, polyvinylidene fluoride, ionomer, acrylonitrile-butadiene-styrene copolymer, polyester such as polyethylene terephthalate (PET), and polybutylene terephthalate (PBT), and fluorine-based resin such as butadiene-styrene copolymer, aromatic or aliphatic polyamide, and polytetrafluoroethylene.

Similar to the belt 21, in the support plate 22, it is preferable that a portion of the support plate 22 overlapping the inflatable portion 40 is substantially transparent. However, without being limited to transparency, the portion may be translucent or colored transparent. In this manner, the puncture site P is reliably visible from the outer surface side, thereby enabling the marker 60 (to be described later) to be rather easily aligned with the puncture site P. The support plate 22 may not have a portion which is not curved like the central portion 22a, that is, the support plate 22 may be curved over the entire length of the support plate 22.

The inflatable portion 40 functions to apply a compressing force to the puncture site P after being inflated by injecting air into the inflatable portion 40. According to the present embodiment, as illustrated in FIGS. 1 and 2, the inflatable portion 40 is configured to include a bag-like or bag-shaped member obtained in such a way that peripheral edges are adhered or welded by overlapping two substantially rectangular sheets with each other and then welding/adhering the peripheral edges of the two sheets to each other. In this manner, an inflatable space 40a is formed between the two sheets. The configuration of the inflatable portion 40 is not particularly limited, as long as the inflatable portion 40 can be inflated by injecting the air. For example, the inflatable portion 40 may be configured to include a bag-like member or bag-shaped obtained in such a way that edge portions are adhered or welded by folding one sheet, or may be configured to include a balloon-like member which does not include the edge portion. In addition, the outer shape of the inflatable portion 40 is not particularly limited. For example, in a state where the inflatable portion 40 is not inflated, the inflatable portion 40 may exhibit an outer shape such as circular, elliptical, and polygonal shapes in a plan view.

As illustrated in FIG. 2, the inflatable portion 40 is located so as to overlap the vicinity between the first curved portion 22b and the central portion 22a of the support plate 22. That is, as shown, the inflatable portion 40 overlaps a part of the first curved portion 22b and a part of the central portion (flat portion) 22a. Therefore, as illustrated in FIG. 9, when the inflatable portion 40 is inflated, the belt 21 and the support plate 22 restrain the inflatable portion 40 from being inflated in a direction away from the body surface side of the wrist W. In this manner, the compressing force of the inflatable portion 40 is concentrated on the wrist W side. Therefore, the puncture site P can be suitably compressed.

In addition, the inflatable portion 40 is attached to the belt 21 of the band 20 via a flexible holder 40b. According to the present embodiment, the holder 40b is configured to include an edge portion on a side having the male side 31 of the Magic Tape® (registered trademark) in the inflatable portion 40. However, the holder 40b may be configured to include a member separate from the inflatable portion 40. In addition, a position for disposing the holder 40b in the inflatable portion 40 and a position for attaching the holder 40b to the band 20 are not particularly limited, as long as the inflatable portion 40 can interlock with the band 20.

The material used to fabricate the inflatable portion 40 is not particularly limited, as long as the material is flexible. For example, it is possible to use a material the same as that of the above-described band 20. In addition, it is preferable that the inflatable portion 40 is configured to include a thermoplastic material which is the same material or the same type as that of the band 20. In this manner, the inflatable portion 40 can be rather easily joined to the band 20 by welding, and the hemostatic device 10 can be rather easily manufactured.

It is preferable that the inflatable portion 40 is substantially transparent. However, without being limited to transparency, the inflatable portion 40 may be translucent or colored transparent. In this manner, the puncture site P is visible from the outer surface side, thereby enabling the marker 60 (to be described later) to easily align with the puncture site P.

The auxiliary compression portion 50 functions to press the inflatable portion 40 as illustrated by an arrow in FIG. 9 so as to adjust a direction of the compressing force applied to the puncture site P by the inflatable portion 40.

Similar to the inflatable portion 40, the auxiliary compression portion 50 is configured to include a bag-like member or bag-shaped member. The auxiliary compression portion 50 may be configured to include a sponge-like substance, an elastic material, an aggregate of fibers such as cotton, or a combination thereof, for example.

The auxiliary compression portion 50 is attached to the inflatable portion 40 so that an internal space of the auxiliary compression portion 50 communicates with the inflatable space 40a of the inflatable portion 40. Therefore, if air is injected into the inflatable portion 40, the auxiliary compression portion 50 is also inflated.

As illustrated in FIG. 3, the marker 60 is disposed at a substantially center on a side facing the band 20 in the inflatable portion 40. Since this marker 60 is disposed in the inflatable portion 40, the inflatable portion 40 can be rather easily aligned with the puncture site P. Accordingly, misalignment of the inflatable portion 40 is restrained. The marker 60 may be disposed on a side facing the wrist W in the inflatable portion 40. In this case, it is preferable that the marker 60 is disposed on an inner surface inside the inflatable portion 40 so as not to directly come into contact with the puncture site P.

Without being particularly limited, a shape of the marker 60 may be circular, triangular, and square shapes, for example. In the present embodiment, the marker 60 has the square shape.

A size of the marker 60 is not particularly limited. However, for example, in a case where the shape of the marker 60 is the square shape, it is preferable that one side length of the square shape marker falls within a range of 1 to 4 mm. If one side length is 5 mm or longer, the size of the marker 60 is larger than the size of the puncture site P. Consequently, the central portion of the inflatable portion 40 is less likely to be aligned with the puncture site P.

Without being particularly limited, a material forming the marker 60 includes oily colorants such as ink, and resins kneaded with pigments.

A color of the marker 60 is not particularly limited, as long as the color enables the inflatable portion 40 to be aligned with the puncture site P. However, it is preferable that the color is a green color system. If the green color system is used, the marker 60 is rather easily visible on the blood or the skin. Accordingly, the inflatable portion 40 is much likely to be aligned with the puncture site P.

In addition, it is preferable that the marker 60 is translucent or colored transparent. In this manner, the puncture site P is visible from the outer surface side of the marker 60.

A method of disposing the marker 60 in the inflatable portion 40 is not particularly limited. However, for example, methods which may be used include a method of printing the marker 60 on the inflatable portion 40, a method of welding the marker 60 to the inflatable portion 40, and a method of bonding the marker 60 to the inflatable portion 40 by applying an adhesive to one side surface of the marker 60.

Figure 4:
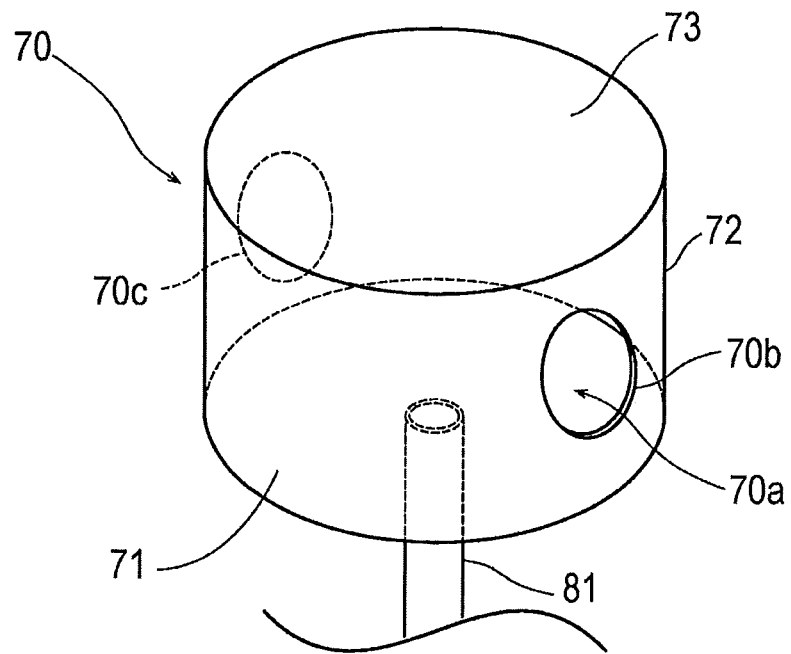
FIG. 4 is a schematic perspective view illustrating an injection part of the hemostatic device according to the embodiment.

The injection part 70 functions to inject the air into the inflatable portion 40. As illustrated in FIGS. 2 and 4, the injection part 70 is configured to include a bag-like member or bag-shaped enclosure including a storage space 70a which can store the air. The injection part 70 is located on the band 20. However, FIG. 4 illustrates the injection part 70 by omitting the band 20.

According to the present embodiment, the injection part 70 includes a bottom face part 71 located on the outer surface side of the band 20, a vertical wall part 72 erected from the bottom face part 71 toward a side where the band 20 is not disposed, and an upper face part 73 connected to the vertical wall part 72 and facing the bottom face part 71. A space surrounded with the bottom face part 71, the vertical wall part 72, and the upper face part 73 corresponds to the storage space 70a. According to the present embodiment, the injection part 70 may be formed to have a cylindrical outer shape. However, the outer shape of the injection part 70 is not particularly limited. For example, the outer shape of the injection part 70 may be a polygonal prism such as a quadrangular prism. Alternatively, the outer shape may be a ball in which the bottom face part, the vertical wall part, and the upper face part are not distinguished from one another.

A volume of the storage space 70a of the injection part 70 is preferably approximately ¼ of a volume of the inflatable space 40a of the inflatable portion 40. In this manner, the injection part 70 is formed to have a proper size, thereby preventing the injection part 70 from interfering with a medical procedure performed around the hemostatic device 10. It is possible to reduce the number of times of injection operations for injecting the air into the inflatable portion 40, which will be described later.

The injection part 70 is located on the outer surface side of the band 20. Therefore, compared to a case where the injection part 70 is disposed so as to protrude from the band 20 to the wrist W side, the injection part 70 is less likely to come into contact with the wrist W of the wearer, and the unpleasant feeling of the wearer can be reduced. In particular, according to the present embodiment, as illustrated in FIG. 2, the injection part 70 is located at a position which does not overlap the inflatable portion 40 in the band 20 and which overlaps the support plate 22. Therefore, even if the injection part 70 is disposed on the band 20, the injection part 70 does not interfere with aligning the inflatable portion 40 with the puncture site P, and the injection operation for injecting the air into the inflatable portion 40 can be performed on the support plate 22 which is relatively rigid. Accordingly, the injection operation is facilitated. A position for locating the injection part 70 is not particularly limited, as long as the injection part 70 is located on the band 20.

Two hole parts 70b and 70c are formed in the injection part 70, penetrate the vertical wall part 72 of the injection part 70 in a direction a1 intersecting a perpendicular line X1 to a region of the band 20 having the injection part 70 and communicate with the storage space 70a. Air can be fetched into or flow into the storage space 70a from these two hole parts 70b and 70c. In this manner, as illustrated in FIG. 8, when the inflatable portion 40 is inflated, the pressing force for crushing or deforming the injection part 70 while closing the hole parts 70b and 70c by the fingers acts in the direction a1 intersecting the perpendicular line X1. Accordingly, the pressing force is relatively less likely to be transmitted to the puncture site P. Therefore, it is possible to suitably prevent a disadvantageous situation where the puncture site P is unnecessarily compressed by the injecting operation for injecting the air into the inflatable portion 40.

In addition, the pressing force for crushing or deforming the injection part 70 while closing the hole parts 70b and 70c by the fingers is relatively less likely to be transmitted to the puncture site P. Accordingly, when the inflatable portion 40 is inflated, the wearer can relatively accurately recognize only the compressing force applied to the puncture site P by the inflatable portion 40. Therefore, based on the compressing force felt by the wearer, it is possible to inject the air into the inflatable portion 40 as much as an optimum amount for performing the hemostasis on the puncture site P.

The two hole parts 70b and 70c are disposed at positions facing each other or opposite one another. FIGS. 8 and 9 show that the two through holes 70b, 70c face each other at positions farther away from the band 20 than the bottom face part 71. Therefore, as illustrated in FIG. 8, in a state where the hole parts 70b and 70c are respectively closed by a thumb and an index finger, the physician or the nurse causes the thumb and the index finger to move close to each other, and to crush the injection part 70. In this manner, the air contained inside the storage space 70a can be injected into the inflatable portion 40. In addition, the injection part 70 has the two hole parts 70b and 70c at positions facing each other. Accordingly, even if one of the hole parts is closed after coming into contact with the surrounding objects, there is a low possibility that the other hole part may be closed. Therefore, even if the injection part 70 is unintentionally crushed or deformed, the injection part 70 has a rather low possibility that the air may be injected into the inflatable portion 40. The number of the hole parts is not particularly limited, as long as the number is 1 or more. In addition, a shape of the hole part is not limited to the illustrated case. In addition, the position for disposing the hole part is not particularly limited, as long as the hole part is formed so as to penetrate the injection part 70 in the direction intersecting the perpendicular line X1 to the band 20.

In order that the injection part 70 can be deflated and can return to the original shape after being deflated, it is preferable that the injection part 70 is configured to include or be made of elastomer materials such as silicone rubber and latex rubber, thermoplastic plastic materials such as polypropylene and polyethylene, or various thermoplastic elastomer materials having both properties of these, for example.

Figure 5:
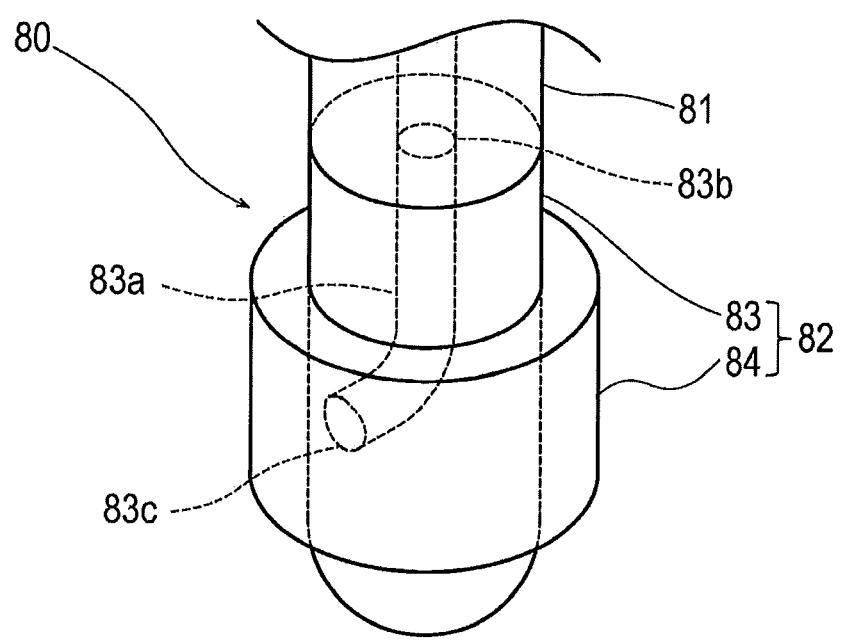
FIG. 5 is a schematic perspective view illustrating a flow route of the hemostatic device according to the embodiment.

As illustrated in FIGS. 2 and 5, the flow route 80 includes a tube 81 (corresponding to a "tubular member") which causes the inflatable space 40a of the inflatable portion 40 and the storage space 70a of the injection part 70 to communicate with each other, and a backflow check structure 82 which prevents the air from flowing out to the injection part 70 from the inflatable portion 40.

A proximal portion of the tube 81 is attached to the bottom face part 71 of the injection part 70, and a distal portion of the tube 81 is attached to the inflatable portion 40 so as to enter the inflatable space 40a of the inflatable portion 40. The position for attaching the tube 81 in the injection part 70 is not particularly limited, as long as the storage space 70a of the injection part 70 and the inflatable space 40a of the inflatable portion 40 can communicate with each other. For example, the proximal portion of the tube 81 may be attached to the vertical wall part 72 of the injection part 70 or the upper face part 73 of the injection part 70.

In addition, as illustrated in FIG. 2, the band 20 is provided with a through-hole, and the tube 81 is located so as to be inserted into the through-hole so that the tube 81 passes through the band 20. Note that, for example, without disposing the through-hole in the band 20, the tube 81 may be located so that the tube 81 turns around the band 20.

The backflow check structure 82 is located inside the inflatable portion 40 and serves as a backflow preventer. As illustrated in FIG. 5, the backflow check structure 82 includes a core 83 connected to the distal portion of the tube 81 and a covering member 84 for covering the core 83.

The core 83 is provided with a substantially cylindrical outer shape. The core 83 has a lumen 83a which is open on a contact surface with the tube 81 and on a surface having the covering member 84. Hereinafter, an opening portion 83b on the contact surface with the tube 81 in the core 83 will be referred to as a "proximal opening portion 83b", and an opening portion (opening) 83c on the surface having the covering member 84 in the core 83 will be referred to as a "distal opening portion 83c".

It is preferable that a material forming the core 83 is a material which is more rigid than that of the covering member 84. For example, the material for fabricating the core 83 includes a known metal material and a plastic material.

The covering member 84 is provided with a cylindrical outer shape. The core 83 is inserted into or positioned in the covering member 84.

It is preferable that a material from which the covering member 84 is made is an elastic material so that the covering member 84 is an elastic member. For example, the material includes elastomer materials such as butyl rubber, polysulfide rubber, epichlorohydrin rubber, high nitrile rubber, fluorine rubber, and silicone rubber, or various thermoplastic elastomer materials.

Figure 6A:
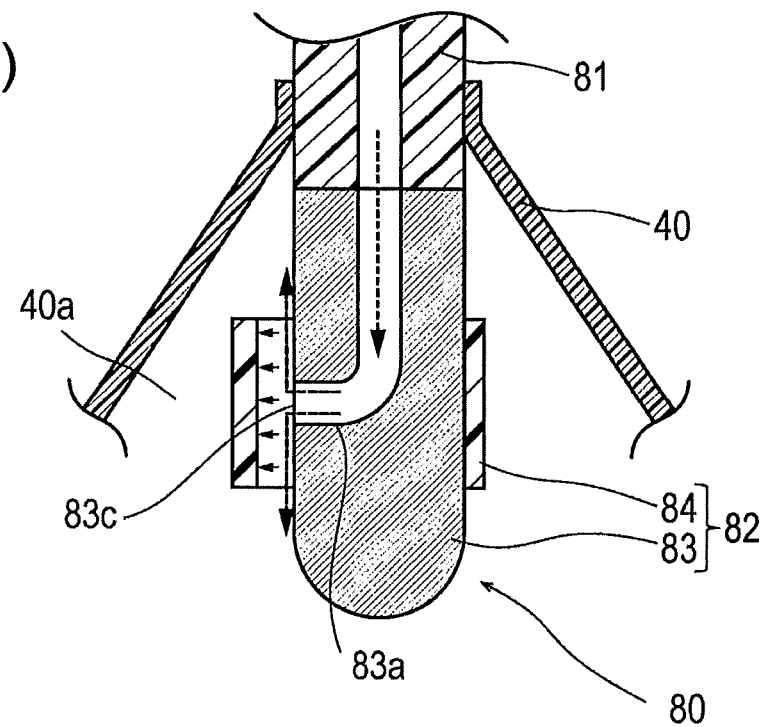
FIGS. 6(A) and 6(B) are enlarged cross-sectional views illustrating a backflow check structure of the hemostatic device according to the embodiment.

In FIG. 6, a dotted line arrow indicates a flow of the air, and a solid line arrow indicates a direction of pressure applied to the covering member by the air. As illustrated in FIG. 6(A), if the air is injected from the injection part 70 into the tube 81 in a state where the inflatable portion 40 is not sufficiently inflated, the air flows through the lumen 83a of the core 83, and applies the pressure to the covering member 84 in a direction away from the core 83. In this manner, the distal opening portion 83c and the inflatable space 40a communicate with each other, and the air is injected into the inflatable portion 40.

Figure 6B:
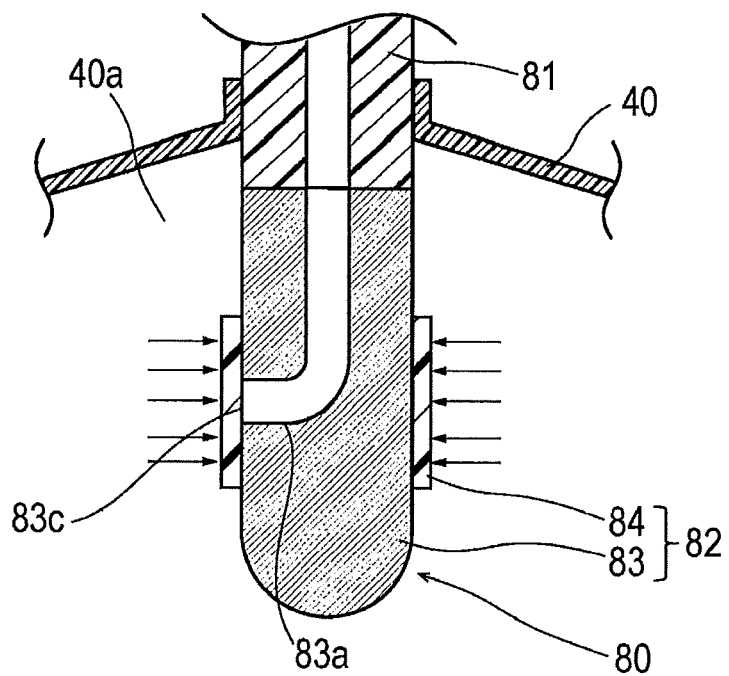

As illustrated in FIG. 6(B), in a state where the inflatable portion 40 is sufficiently inflated, the air contained inside the inflatable portion 40 applies the pressure to the covering member 84 in a direction for coming into contact with the core 83. In this manner, the distal opening portion 83c is closed by the covering member 84. Accordingly, the air contained inside the inflatable portion 40 does not flow back not only to the core 83 side but also to the injection part 70 side. In addition, in a state where the inflatable portion 40 is sufficiently inflated, the air contained inside the inflatable portion 40 applies the pressure to the covering member 84 so as to close the distal opening portion 83c, and the pressure is higher than injecting pressure of the air. Therefore, if the inflatable portion 40 is sufficiently inflated and the internal pressure of the inflatable portion 40 reaches a predetermined value, the air cannot be injected into the inflatable portion 40 from the injection part 70. In this manner, in a state where the inflatable portion 40 is sufficiently inflated, it is possible to suitably prevent the puncture site P from being unnecessarily compressed after the air is unnecessarily injected into the inflatable portion 40 and the inflatable portion 40 is excessively inflated.

The discharge portion 90 functions to discharge the air contained inside the inflatable portion 40 outward. As illustrated in FIG. 3, the discharge portion 90 includes a discharge port 91 located on the band 20, a tube 92 which communicates the internal space of the discharge port 91 and the inflatable space 40a of the inflatable portion 40 with each other, a valve 93 which can prevent the air contained inside the inflatable portion 40 from being discharged outward, a switching member 94 which can switch communication and communication cancellation between the internal space of the discharge port 91 and the outside, and an interlock member 95 which prevents the switching member 94 from falling out or becoming separated from the discharge port 91.

As illustrated in FIGS. 1 and 3, the discharge port 91 is provided with a cylindrical outer shape. However, without being particularly limited, the outer shape of the discharge port 91 may be a sphere or a polygonal prism such as a quadrangular prism, for example.

The discharge port 91 is located on the outer surface side of the band 20. Therefore, compared to a case where the discharge port 91 is disposed so as to protrude from the band 20 toward the wrist W side, the discharge port 91 is less likely to come into contact with the wrist W of the wearer, and the unpleasant feeling of the wearer can be reduced. In particular, according to the present embodiment, the discharge port 91 on the outer surface side of the band 20 is provided at a position that does not overlap the inflatable portion 40 but overlaps the support plate 22. Therefore, even if the discharge port 91 is disposed on the band 20, the discharge port 91 does not interfere with aligning the inflatable portion 40 with the puncture site P, and the switching member 94 (to be described later) is attached and detached on the support plate 22 which is very rigid. Accordingly, an operation for attaching and detaching the switching member 94 is facilitated. However, the position of the discharge port 91 in the band 20 is not particularly limited.

Figure 11:
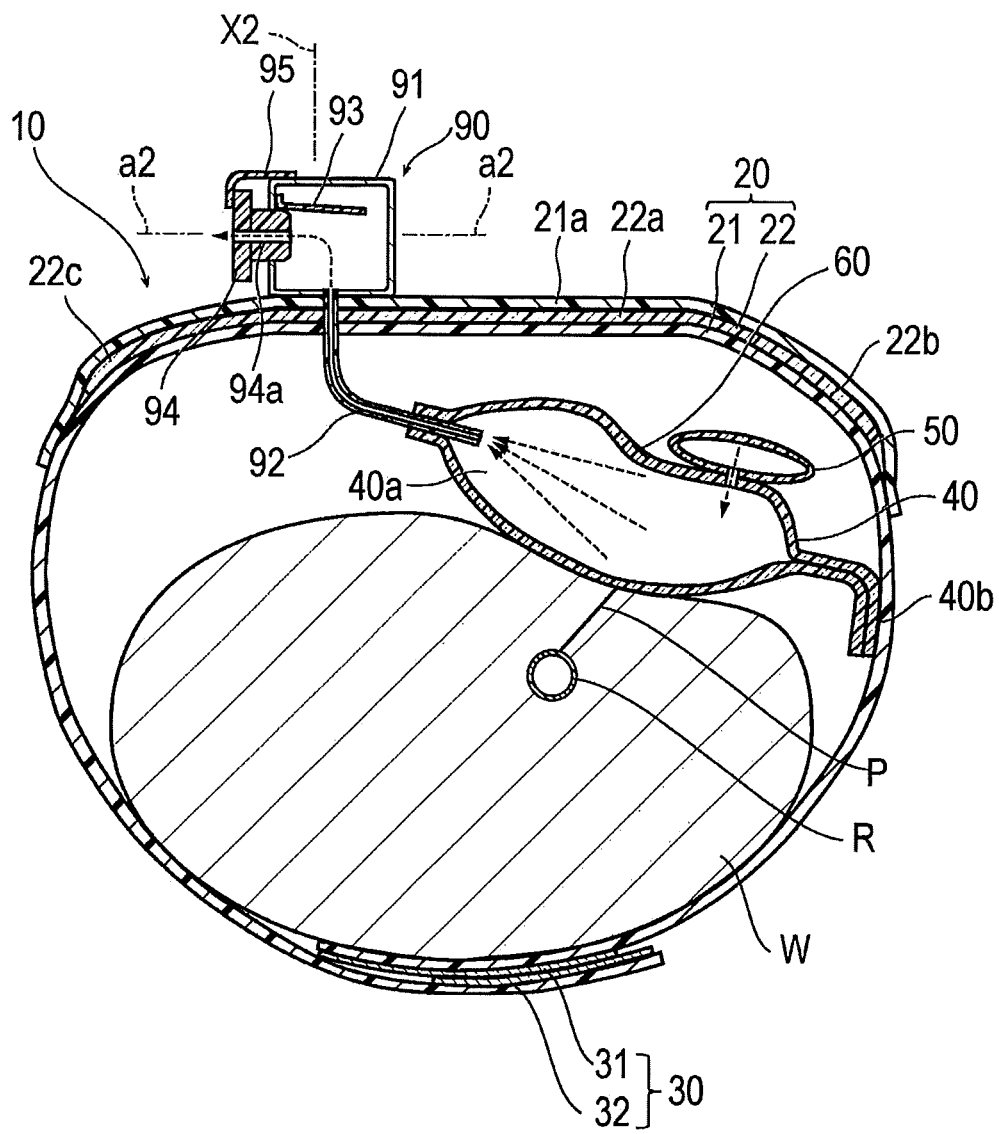
FIG. 11 is a cross-sectional view taken along line 10-10 in FIG. 7, and is a view illustrating a state where the inflatable portion is deflated.

The discharge port 91 has a through-hole 91a penetrating the discharge port 91 in the thickness direction. As illustrated in FIG. 3, it is preferable that the through-hole 91a penetrates the discharge port 91 in a direction a2 intersecting a perpendicular line X2 to a region of the band 20 having the discharge portion 90. In this manner, as illustrated in FIG. 11, a pushing force for pushing the switching member 94 into the through-hole 91a acts in the direction a2 intersecting the perpendicular line X2, and the pushing force is less likely to be transmitted to the puncture site P. Therefore, it is possible to prevent a disadvantageous situation where the puncture site P is unnecessarily compressed.

In order to prevent a disadvantageous situation where the air contained inside the discharge port 91 flows back to the inflatable portion 40 after the discharge port 91 is crushed and unintentionally contracted, it is preferable that the discharge port 91 is formed of a material which is relatively rigid so that a constant shape of the discharge port 91 can be maintained. As this material, for example, a material the same as that of the support plate 22 can be used.

The valve 93 is located on the inner surface side of the discharge port 91 so as to close the through-hole 91a. Only a portion of the peripheral edge portion of the valve 93 is attached to the inner surface side of the discharge port 91. Therefore, as illustrated in FIG. 11, the switching member 94 can be inserted into the through-hole 91a.

It is preferable that the valve 93 is configured to include a flexible material. For example, a material the same as that of the band 20 can be used to fabricate the valve 93.

The switching member 94 is configured so as to be removable from the through-hole 91a. According to the present embodiment, the switching member 94 is provided with a shape in which two cylinders having different diameters are coaxially arrayed side by side. In the switching member 94, a cylindrical portion having a small diameter is inserted into the through-hole 91a of the discharge port 91. In a state where the switching member 94 is inserted into or positioned in the through-hole 91a, a cylindrical portion having a large diameter in the switching member 94 is in a state of protruding outward from the discharge port 91. The switching member 94 can be removed from the through-hole 91a by pulling this protruding portion. The shape of the switching member 94 is not particularly limited, as long as the switching member 94 can be removed from the through-hole 91a.

In addition, the switching member 94 has a discharge lumen 94a penetrating or passing through the switching member 94 in the axial direction.

Figure 10:
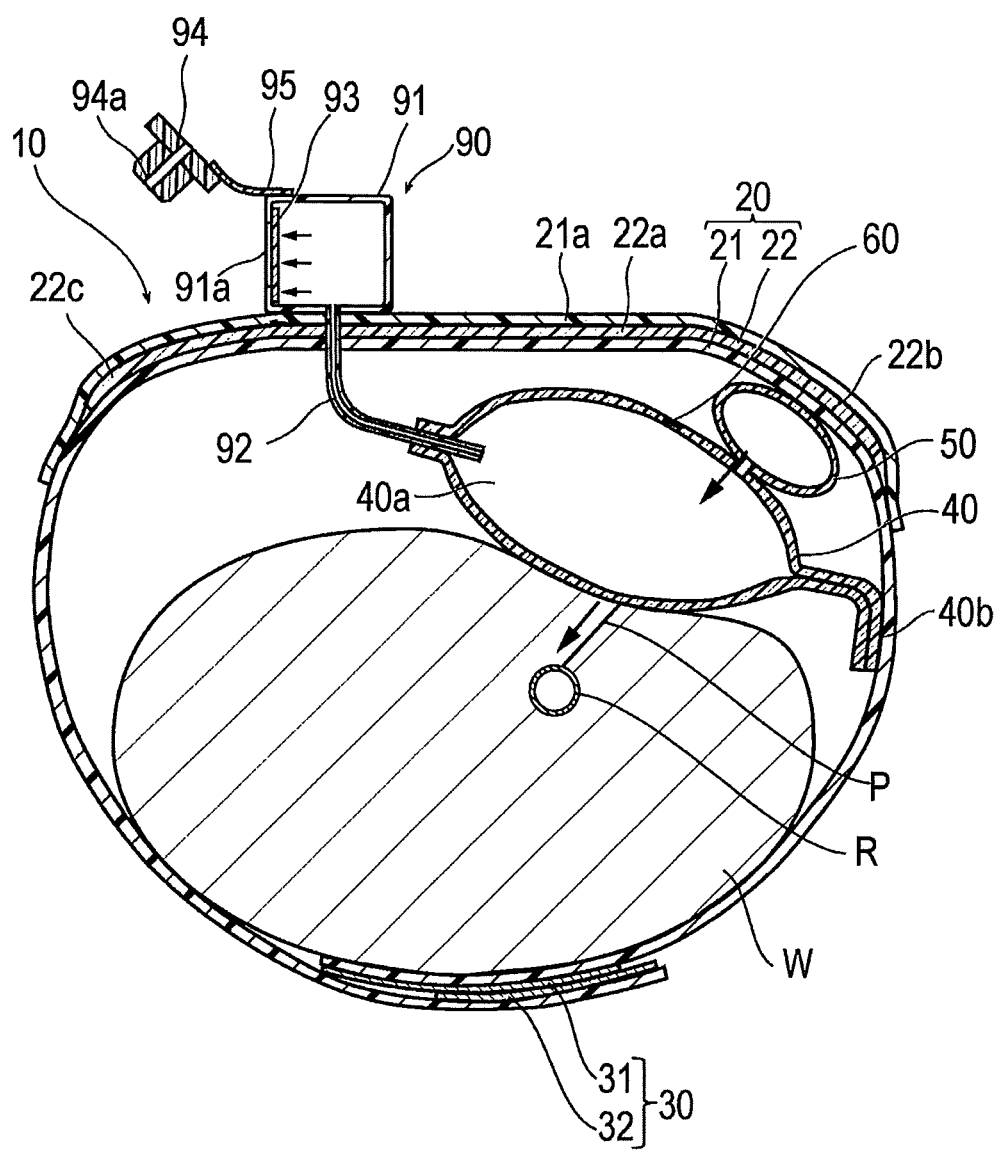
FIG. 10 is a cross-sectional view taken along line 10-10 in FIG. 7, and is a view illustrating a state where the inflatable portion is completely inflated.

As illustrated in FIG. 10, in a state where the switching member 94 is not inserted into the through-hole 91a of the discharge port 91, the through-hole 91a is closed by the valve 93. Therefore, the air contained inside the inflatable portion 40 is not discharged outward.

As illustrated in FIG. 11, in a state where the switching member 94 is inserted into the through-hole 91a of the discharge port 91, the internal space of the discharge port 91 and the outside communicate with each other by the discharge lumen 94a of the switching member 94, and the air contained inside the inflatable portion 40 is discharged outward.

It is preferable that the interlock member 95 is configured to include a flexible material. For example, a material the same as that of the band 20 can be used.

Next, one example of a manner of using the hemostatic device 10 according to the present embodiment will be described.

Before the hemostatic device 10 is worn on the wrist W, the inflatable portion 40 is in a non-inflated state as illustrated in FIG. 2. As illustrated in FIGS. 7 and 8, in a case where the radial artery R of the wrist W of the right hand is punctured, the puncture site P is located at a position close to a thumb side. Normally, the introducer sheath is indwelled at the puncture site P. The band 20 is wrapped around the wrist W in a state in which the introducer sheath is indwelled at the puncture site P. The inflatable portion 40 and the band 20 are aligned so that the marker 60 disposed in the inflatable portion 40 overlaps the puncture site P from above. The male side 31 and the female side 32 of the surface fastener 30 are brought into contact with and joined to each other. In this manner, the band 20 is worn and held on the wrist W.

After the hemostatic device 10 is applied to the wrist W and while the hemostatic device 10 is worn on or secured in place on the wrist W, the injection part 70 is crushed while the hole parts 70b and 70c of the injection part 70 are closed by the fingers as illustrated in FIG. 8. The air contained inside the injection part 70 is injected into the inflatable portion 40 so as to inflate the inflatable portion 40 and the auxiliary compression portion 50. The inflatable portion 40 is inflated by the injection part 70 integrated with the inflatable portion 40. Accordingly, the physician or the nurse does not need to carry a separate and dedicated instrument (such as a syringe) for inflating the inflatable portion 40.

After the inflatable portion 40 is inflated, the introducer sheath is removed from the puncture site P.

After the introducer sheath is removed, depending on a progress condition (i.e., the progress of the patient's condition) or an elapsed time of the hemostasis, an air volume supplied to the inflatable portion 40 and the auxiliary compression portion 50 may be adjusted by the injection part 70 and the discharge portion 90, and the compressing force applied to the puncture site P by the inflatable portion 40 may be adjusted. For example, if the inflated inflatable portion 40 continues to compress the puncture site P and a blood vessel or a nerve around the puncture site for a relatively long time, there is a possibility that numbness or pain may be caused or the blood vessel may be occluded. In order to prevent the vascular occlusion, after the inflatable portion 40 is inflated, the air contained inside the inflatable portion 40 is expelled by the discharge portion 90 with the lapse of time (i.e., over time), and a decompressing operation is performed so as to gradually reduce the internal pressure of the inflatable portion 40. In this manner, the compressing force acting on the puncture site P may be reduced over time. In this way, the decompressing operation can be performed by the discharge portion 90. Accordingly, the physician or the nurse can save labor and time for carrying the dedicated instrument (such as a syringe) in order to perform the decompressing operation.

If the hemostasis is completely performed on the puncture site P after a predetermined period of time elapses, the hemostatic device 10 is detached. The hemostatic device 10 is detached from the wrist W by separating the male side 31 and the female side 32 of the surface fastener 30 from each other. After the air contained inside the inflatable portion 40 is expelled by the discharge portion 90, the hemostatic device 10 may be detached.

As described above, the hemostatic device 10 according to the present embodiment has the band 20 for being wrapped around the wrist W, the means 30 for securing the band 20 in a state where the band 20 is wrapped around the wrist W, the inflatable portion 40 that is inflated by injecting air to compress the puncture site P, the injection part 70 that includes the storage space 70a capable of storing the air, and that can inject the air stored in the storage space 70a into the inflatable portion 40, and the flow route 80 which causes the inflatable portion 40 and the injection part 70 to communicate with each other. The flow route 80 includes the backflow check structure 82 which prevents the air from flowing out to the injection part 70 from the inflatable portion 40. The injection part 70 is located on the band 20, and includes the hole parts 70b and 70c penetrating the injection part 70 in the direction a1 intersecting the perpendicular line X1 to the region of the band 20 having the injection part 70 and communicating with the storage space 70a.

According to the hemostatic device 10 configured in this way, air is injected into the inflatable portion 40 by the injection part 70 communicating with the inflatable portion 40. Therefore, the physician or the nurse can inflate the inflatable portion 40 without using or requiring a separate dedicated instrument. In addition, the injection part 70 is located on the band 20 and is less likely to come into contact with the wrist W. Accordingly, the unpleasant feeling of the wearer can be reduced. In addition, the hole parts 70b and 70c penetrate the injection part 70 in the direction a1 intersecting the perpendicular line X1 to the region of the band 20 having the injection part 70. Therefore, the direction of the pressing force when the injection part 70 is pressed in a state where the hole parts 70b and 70c are closed by the fingers is the direction a1 intersecting the perpendicular line X1 to the band 20. Therefore, the pressing force is less likely to be transmitted to the puncture site P. In addition, there is a low possibility that the hole parts 70b and 70c are closed by coming into contact with the surrounding objects. Accordingly, there is low possibility that the air may be injected into the inflatable portion 40 after the injection part 70 is crushed in a state where the hole parts 70b and 70c are unintentionally closed. Therefore, it is possible to suitably prevent a disadvantageous situation where the puncture site P is unnecessarily compressed.

In addition, the band 20 includes the inner surface on the inflatable portion 40 side and the outer surface facing the inner surface, and the injection part 70 is located on the outer surface. Therefore, the injection operation for injecting the air into the inflatable portion 40 can be facilitated by the injection part 70.

Also, the band 20 includes the support plate 22, and the injection part 70 is located in the region of the band 20 where the support plate 22 is positioned. The injection operation for injecting air into the inflatable portion 40 can be facilitated by the injection part 70.

In addition, the flow route 80 includes the tube 81 which causes the inflatable portion 40 and the injection part 70 to communicate with each other, and one end portion of the tube 81 is located inside the inflatable portion 40, and the backflow check structure 82 is located inside the inflatable portion 40. Therefore, air can be more suitably delivered into the inflatable portion 40. In addition, it is possible to prevent the air from flowing back to the tube 81.

The injection part 70 includes the bottom face part 71 located on the second surface side of the band 20, the vertical wall part 72 erected or projecting from the bottom face part 71 toward a side where the band 20 is not disposed, and the upper face part 73 connected to the vertical wall part 72. The storage space 70a is surrounded with the bottom face part 71, the vertical wall part 72, and the upper face part 73, and the hole parts 70b and 70c are disposed in the vertical wall part 72. Therefore, there is a much lower possibility that the hole parts 70b and 70c may be closed by coming into contact with the surrounding objects. In addition, the direction of the pressing force when the injection part 70 is pressed while the hole parts 70b and 70c are closed by the fingers is the direction a1 intersecting the perpendicular line X1 to the band 20. Accordingly, the pressing force is much less likely to be transmitted to the puncture site P. Therefore, it is possible to more suitably prevent a disadvantageous situation where the puncture site P is excessively compressed.

Modification Example 1

Figure 12:
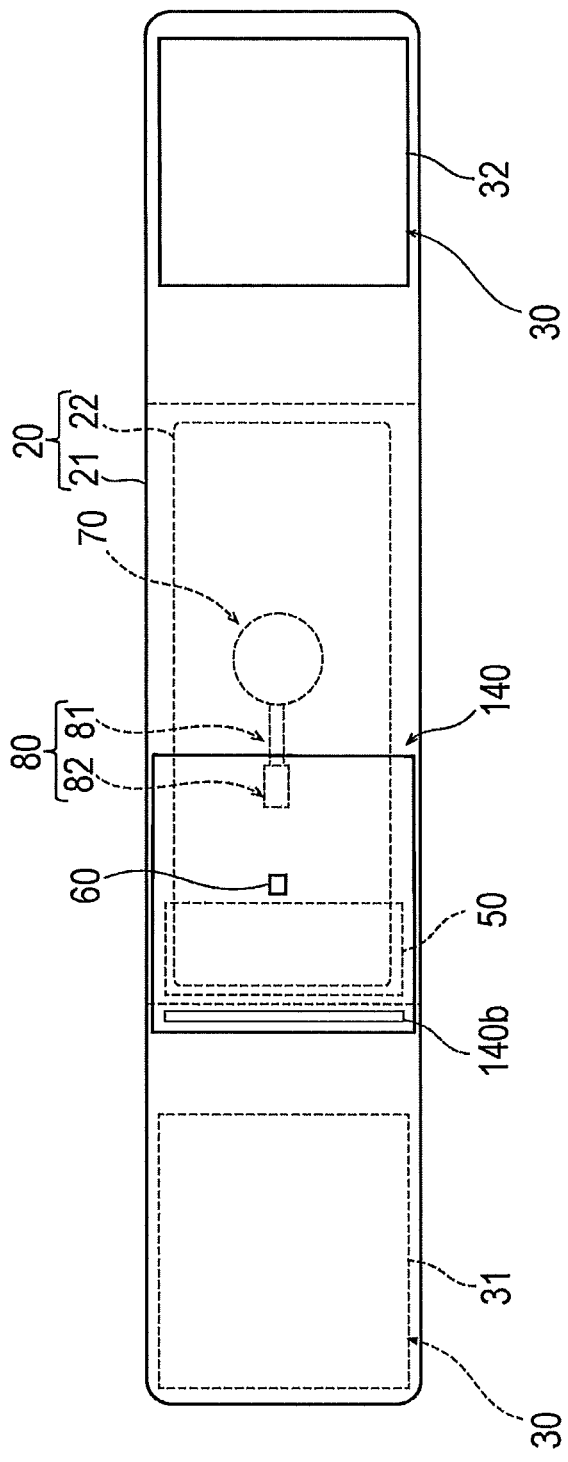
FIG. 12 is a plan view when a hemostatic device according to Modification Example 1 of the embodiment is viewed from the inner surface side.
Figure 13A:
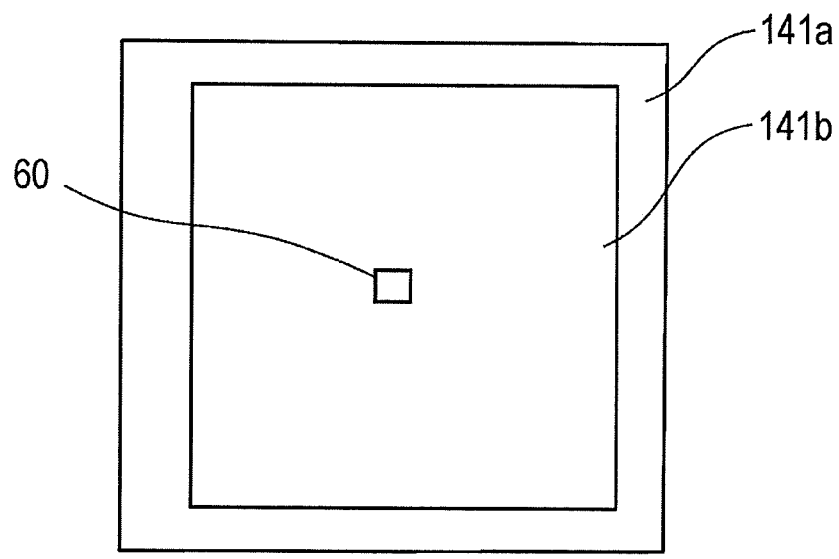
FIGS. 13(A) and 13(B) are plan views illustrating a configuration of an inflatable portion of the hemostatic device according to Modification Example 1 of the embodiment.
Figure 13B:
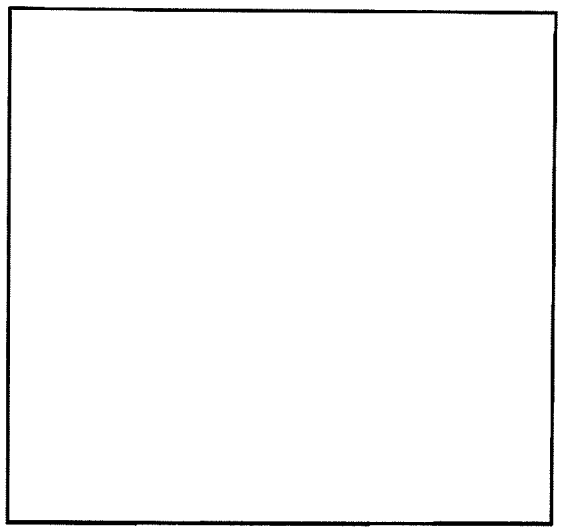
Figure 14:
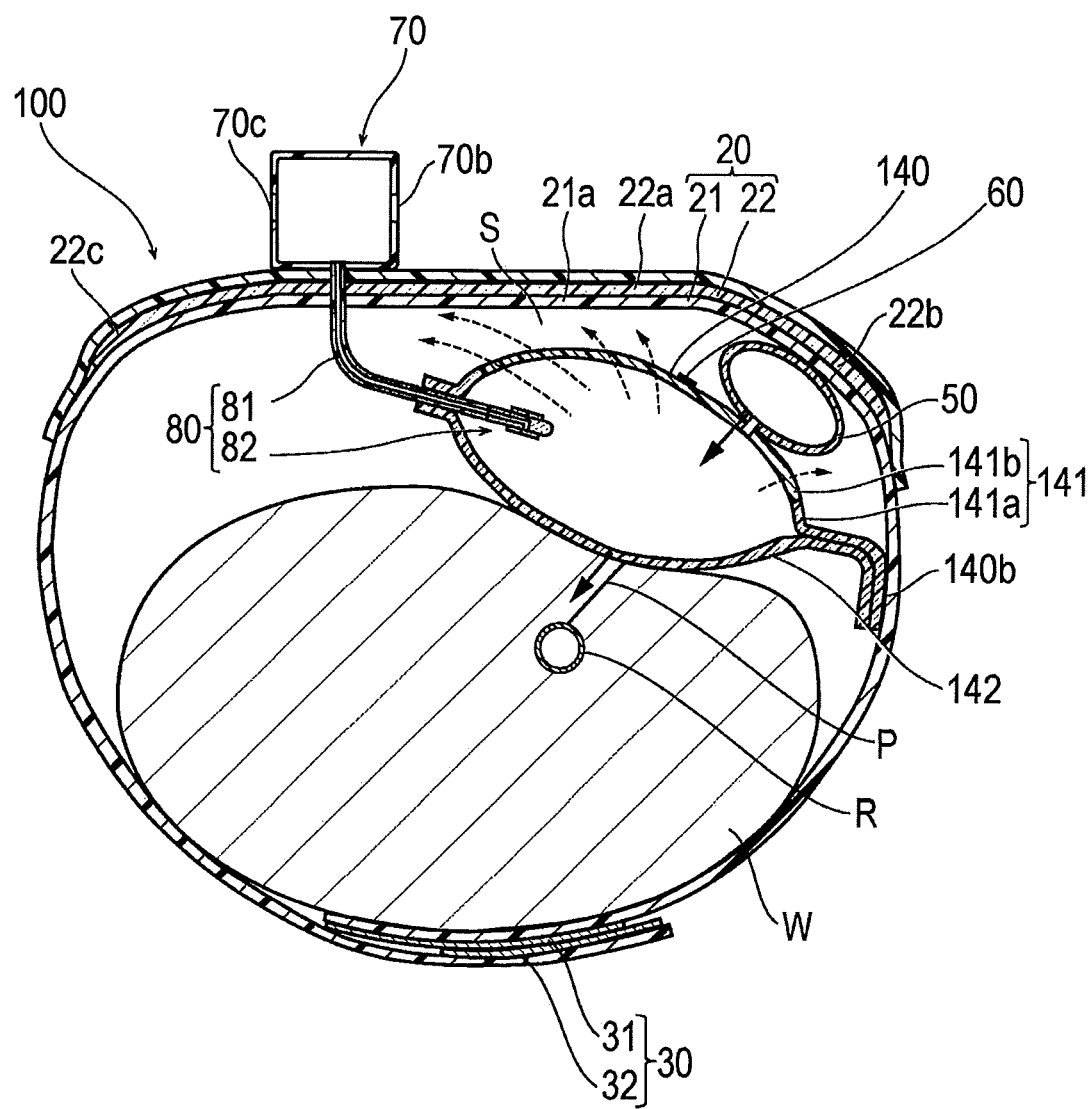
FIG. 14 is a schematic cross-sectional view illustrating a state where the hemostatic device according to Modification Example 1 of the embodiment is worn on a wrist.

FIGS. 12 to 14 are views for describing a hemostatic device 100 according to Modification Example 1 of the above-described embodiment. Hereinafter, the hemostatic device 100 according to Modification Example 1 will be described with reference to FIGS. 12 to 14. In the description below, features that are the same or similar to those described above are identified by the same reference numerals and a detailed description of such features is not repeated.

The hemostatic device 100 according to Modification Example 1 is different from that according to the above-described embodiment in that an inflatable portion 140 also functions as the discharge portion for discharging the air contained inside the inflatable portion 140 outward.

As illustrated in FIGS. 12 to 14, the inflatable portion 140 is configured to have a bag shape produced by overlapping a first sheet 141 and a second sheet 142 which have a substantially rectangular shape.

As illustrated in FIG. 13(A), the first sheet 141 includes a peripheral edge portion 141a configured to include a thermoplastic material and a central portion 141b configured to include or be fabricated from a thermosetting elastomer.

According to the present embodiment, the first sheet 141 is formed as follows. The thermoplastic material and the thermosetting elastomer are respectively poured into predetermined positions of a mold having a predetermined shape, and then integrally molded. However, the first sheet 141 may alternatively be formed as follows. A rectangular member (corresponding to the "central portion 141b") configured to include the thermosetting elastomer is located at the center of a frame-shaped member (corresponding to the "peripheral edge portion 141a") configured to include the thermoplastic material, and both of these are adhered to each other using an adhesive.

The second sheet 142 is configured to include or be fabricated from the thermoplastic material.

As illustrated in FIG. 14, a portion where the peripheral edge portion 141a of the first sheet 141 and a peripheral edge portion of the second sheet 142 overlap each other is welded.

One side 140b in the peripheral edge portion 141a of the first sheet 141 is welded to a side where the belt 21 of the band 20 faces the wrist W.

The thermoplastic material used for fabricating the inflatable portion 140 is not particularly limited. However, it is possible to use a thermoplastic resin such as polyvinyl chloride, polyethylene, polypropylene, and polyvinylidene chloride, or various thermoplastic elastomers such as an olefinic thermoplastic elastomer, a styrene thermoplastic elastomer and a polyethylene thermoplastic elastomer.

As the thermosetting elastomer used for the inflatable portion 140, those which have gas permeability higher than that of the thermoplastic material used for the inflatable portion 140 are used. For example, as the material, it is possible to use silicone or natural rubber. Therefore, in the inflatable portion 140, after the inflatable portion 140 is inflated, the gas contained inside the inflatable portion 140 is discharged outward of the inflatable portion 140 with the lapse of time via the region formed of the thermosetting elastomer in the inflatable portion 140 to such an extent that the vascular occlusion can be prevented (illustrated by a dotted line arrow in FIG. 14).

As described above, according to the hemostatic device 100 in Modification Example 1, the gas contained inside the inflatable portion 140 is discharged outward of the inflatable portion 140 over time via the region formed of the thermosetting elastomer in the inflatable portion 140 to such an extent that the vascular occlusion can be prevented. Accordingly, even if the physician or the nurse does not perform the decompressing operation, the compressing force applied to the puncture site P can be reduced with the passage of time to such an extent that the vascular occlusion can be prevented. Therefore, the treatment burden on the physician or the nurse and labor cost can be reduced.

In addition, the central portion formed of the thermosetting elastomer on the band 20 side in the inflatable portion 140 is most likely to stretch. When the inflatable portion 140 is inflated, the central portion of the inflatable portion 140 located at a position corresponding to the puncture site P is inflated most. Accordingly, the puncture site P can be suitably compressed. Note that, the thermosetting elastomer may be disposed in the central portion of the inflatable portion 140 on the wrist W side.

In addition, the region formed of the thermosetting elastomer in the inflatable portion 140 is disposed on the side facing the band 20, and the auxiliary compression portion 50 is disposed between the region formed of the thermosetting elastomer and the band 20. Therefore, since a space S is formed between the inflatable portion 140 and the band 20, it is possible to increase the area of the portion exposed without coming into contact with the band 20 in the region formed of the thermosetting elastomer of the inflatable portion 140. Therefore, the gas can be more satisfactorily discharged from this exposed portion.

Modification Example 2

Figure 15:
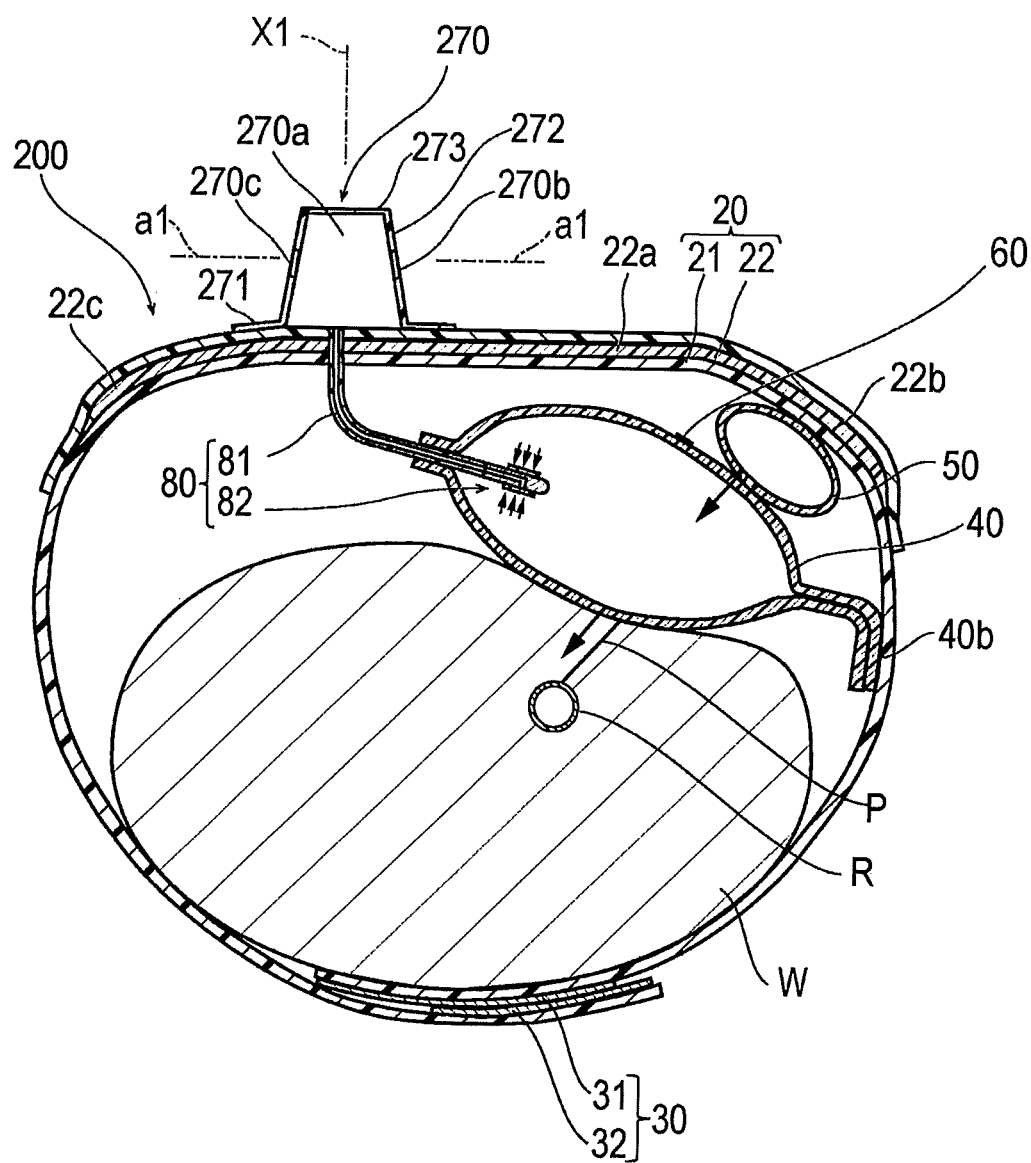
FIG. 15 is a schematic cross-sectional view illustrating a hemostatic device according to Modification Example 2 of the embodiment.

FIG. 15 is a view for describing a hemostatic device 200 according to Modification Example 2 of the above-described embodiment. Hereinafter, the hemostatic device 200 according to the Modification Example 2 will be described with reference to FIG. 15. In the following description, features that are the same or similar to those described above are identified by the same reference numerals and a detailed description of such features is not repeated.

The hemostatic device 200 according to Modification Example 2 is different from that according to the above-described embodiment in that a storage space 270a of an injection part 270 is surrounded with the band 20, a vertical wall part 272, and an upper face part 273.

The injection part 270 includes a bottom face part 271 located on the outer surface side of the band 20, the vertical wall part 272 erected from (projecting away from) the bottom face part 271 toward the side where the band 20 is not disposed, and the upper face part 273 connected to the vertical wall part 272. As a material for forming or fabricating the injection part 270, it is possible to use a material the same as that according to the above-described embodiment.

The bottom face part 271 is attached to the band 20 on the outer side (on a side opposite to a region having the storage space 270a) of the vertical wall part 272. Therefore, the space surrounded by the band 20, the vertical wall part 272, and the upper face part 273 corresponds to or constitutes the storage space 270a.

The vertical wall part 272 is inclined with respect to the outer surface of the band 20 so that the width of the storage space 270a decreases (tapers) along the direction from the band 20 toward the upper face part 273. The vertical wall part 272 may be erected or extend vertically (i.e., in a non-tapering manner) from the bottom face part 271.

The vertical wall part 272 has two hole parts 270b and 270c penetrating the vertical wall part 272 in the thickness direction, that is, in the direction a1 intersecting the perpendicular line X1 to the region of the band 20 having the injection part 270. The hole parts 270b and 270c are disposed at positions facing each other. The hole parts 270b and 270c communicate with the storage space 270a.

As described above, according to the hemostatic device 200 in Modification Example 2, the injection part 270 includes the bottom face part 271 located on the outer surface side of the band 20, the vertical wall part 272 extending from the bottom face part 271 toward the side where the band 20 is not disposed, and the upper face part 273 connected to the vertical wall part 272. The storage space 270a is surrounded with the band 20, the vertical wall part 272, and the upper face part 273, and the hole parts 270b and 270c are disposed in the vertical wall part 272. Therefore, there is a much lower possibility that the hole parts 270b and 270c are closed by coming into contact with the surrounding objects. In addition, the direction of the pressing force when the injection part 270 is pressed while the hole parts 270b and 270c are closed by the fingers is the direction a1 intersecting the perpendicular line X1 to the band 20. Accordingly, the pressing force is much less likely to be transmitted to the puncture site P. Therefore, it is possible to more suitably prevent a disadvantageous situation where the puncture site P is excessively compressed.

The description above describes versions of a hemostatic device representing examples of the inventive hemostatic device. However, without being limited to only the respectively described configurations, the present invention can be appropriately modified, while still falling within the scope of the appended claims.

For example, each portion configuring the hemostatic device can be substituted with any desired configuration which can fulfill the same function. In addition, any desired configuration element may be added to the hemostatic device.

In addition, without being limited to the hemostatic device used by being worn on the wrist, the present invention is also applicable to a hemostatic device used by being worn on a leg.

In addition, in the above-described embodiment, a case has been described where the hemostatic device includes the auxiliary compression portion. However, the hemostatic device may not include the auxiliary compression portion.

In addition, in the above-described embodiment, the inflatable portion interlocks with the band. However, the inflatable portion may not directly interlock with the band. For example, the flow route may be disposed so as to penetrate the band, the inflatable portion may be connected to the end portion of the inner surface side of the flow route, and the injection part may be connected to the end portion of the outer surface side of the flow route so that the inflatable portion does not fall out from the band.

In addition, in the above-described embodiment, an example has been described where the backflow check structure is disposed inside the inflatable portion. However, the position for locating the backflow check structure is not limited, as long as the backflow check structure is located at any position between the inside of the inflatable portion and the injection part. In addition, depending on the locating position, the configuration of the backflow check structure can be appropriately changed.

In addition, in the above-described embodiment, an example has been described where the hemostatic device includes the discharge portion. However, the hemostatic device may not include the discharge portion. In addition, in a case where the hemostatic device includes the discharge portion, the configuration, the locating position, and the shape of the discharge portion are not limited to the above-described embodiment, as long as the gas contained inside the inflatable portion can be discharged outward. For example, according to Modification Example 1 of the above-described embodiment, the region formed of the thermosetting elastomer is disposed in the central portion of the inflatable portion. However, the region for disposing the thermosetting elastomer is not particularly limited. The whole inflatable portion may be configured to include the thermosetting elastomer. In addition, for example, the hemostatic device may include both the discharge portion configured to include the discharge port according to the above-described embodiment and the inflatable portion including the region formed of the thermosetting elastomer.

The detailed description above describes embodiments of a catheter and operational method representing examples of the inventive catheter and operation disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
    a band for being wrapped around a portion of a limb at which is located a site where bleeding is to be stopped;
    means for securing the band in a wrapped state in which the band is wrapped around the limb;
    an inflatable portion that is inflatable upon injecting gas into the inflatable portion and that compresses the site where bleeding is to be stopped when the inflatable portion is inflated;
    an injection part that includes a storage space configured to store the gas to be injected into the inflatable portion, wherein the injection part is configured to inject the gas into the inflatable portion;
    a flow route configured to communicate the inflatable portion and the injection part with each other;
    wherein the flow route includes a backflow check structure which prevents the gas from flowing out to the injection part from the inflatable portion;
    wherein the band includes a first surface located on one side of the band and a second surface on an opposite side of the band;
    wherein the injection part includes a bottom face part located on the second surface of the band, a vertical wall part extending away from the bottom face part and the second surface of the band, and an upper face part connected to the vertical wall part;
    wherein the storage space is surrounded by the vertical wall part, the upper face part and either the band or the bottom face part; and
    wherein the injection part includes a hole that is disposed in the vertical wall part and that communicates with the storage space.

2. The hemostatic device according to claim 1, wherein the inflatable portion is located on the first surface of the band.

3. The hemostatic device according to claim 1, wherein the band includes a support plate, and the injection part is located in a region of the band where the support plate is positioned.

4. The hemostatic device according to claim 1, wherein the flow route includes a tubular member communicating the inflatable portion and the injection part to each other;

the tubular member including one end portion positioned inside the inflatable portion; and the backflow check structure is located inside the inflatable portion.

5. The hemostatic device according to claim 1, wherein the flow route comprises a tube that includes a lumen extending throughout the tube, wherein one end of the lumen terminates at one opening located inside the inflatable portion, and an opposite end of the lumen terminates at another opening that opens into the injection part.

6. The hemostatic device according to claim 1, wherein the flow route comprises a tube that includes a lumen terminating at respective openings, wherein the backflow check structure includes a covering member that covers one of the openings and prevents communication between the storage space and the inflatable portion before the gas is injected from the storage space into the inflatable portion, wherein the covering member is moved away from the one of the openings when the gas is injected from the storage space into the inflatable portion.

7. A hemostatic device comprising:

a band configured to be wrapped around a portion of a limb at which is located a site where bleeding is to be stopped;

means for securing the band in a wrapped state where the band is wrapped around the limb;

an inflatable portion that is inflatable upon injecting gas into the inflatable portion and that compresses the site where bleeding is to be stopped when the inflatable portion is inflated;

an injection part that includes a storage space configured to store the gas to be injected into the inflatable portion and that is configured to inject the gas into the inflatable portion;

a lumen extending between the inflatable portion and the injection part to communicate the inflatable portion with the injection part;

a backflow preventer that prevents the gas in the inflatable portion from flowing to the injection part by way of the lumen;

the injection part including a bottom face part secured to an outer surface of the band that faces away from the limb when the band is in the wrapped state;

the injection part including two spaced apart through holes communicating the storage space with a region outside the storage space; and the two through holes facing each other at positions farther away from the band than the bottom face part;

the injection part including an upper face part positioned in opposing relation to the bottom face part; and the injection part including a wall extending between the upper face part and the bottom face part, wherein the two through holes pass through the wall.

8. The hemostatic device according to claim 7, wherein the lumen is located in a tube and terminates at one end in a first opening that is located in the inflatable portion and terminates at an opposite end in a second opening that opens into the injection part.

9. The hemostatic device according to claim 7, wherein the lumen terminates at respective openings, the backflow preventer being an elastic member that covers one of the openings to prevent communication between the storage space and the inflatable portion before the gas is injected from the storage space into the inflatable portion, the elastic member being moved away from the one of the openings when the gas is injected from the storage space into the inflatable portion.

10. The hemostatic device according to claim 7, wherein the band includes a first surface that faces the limb when the band is in the wrapped state.

11. The hemostatic device according to claim 7, wherein the band includes a belt and a support plate, the support plate being more rigid than the belt, the injection part being fixed to the band at a location overlapping the support plate.

12. The hemostatic device according to claim 7, wherein the lumen is positioned inside a tubular member connected to both the inflatable portion and the injection part, one end portion of the tubular member being positioned inside the inflatable portion, and the backflow preventer being located inside the inflatable portion.

13. The hemostatic device according to claim 7, wherein the lumen is positioned inside a tubular member, the tubular member passing through the band.

14. The hemostatic device according to claim 7, wherein the band includes a belt and a support plate, the support plate being more rigid than the belt, the lumen being positioned inside a tubular member, the tubular member passing through the belt and the plate.

15. The hemostatic device according to claim 7, wherein the lumen is located in a tube and includes opposite open ends, the backflow preventer being an elastic member that covers one of the open ends.

16. A method comprising:

wrapping a band around a portion of a limb at which is located a site where bleeding is to be stopped so that an inflatable portion overlies the site and is positioned between the limb and an inner surface of the band that faces the limb;

securing the band in a wrapped state around the limb while the inflatable portion remains overlying the site and positioned between the limb and the band;

applying a pressing force to an injection part that is in communication with the inflatable portion to compress the injection part and cause gas in the injection part to flow into the inflatable portion to inflate the inflatable portion and apply a compressive force to the site where bleeding is to be stopped, the injection part being fixed to an outer surface of the band that faces away from the limb in the wrapped state of the band;

wherein the applying of the pressing force to the injection part comprises applying the pressing force to opposite sides of the injection part in a direction intersecting an axis perpendicular to the band; and wherein the applying of the pressing force to the injection part comprises covering two through holes passing through a wall of the injection part that surrounds a space containing the gas, the covering of the two through holes being performed while compressing the injection part.

17. The method according to claim 16, further comprising preventing a backward flow of gas from the inflatable portion to the injection part.

* * * * *